United States Patent [19]

Hart et al.

[11] Patent Number: 5,618,837

[45] Date of Patent: Apr. 8, 1997

[54] PDGF ANTAGONISTS III

[75] Inventors: Charles E. Hart, Brier, Wash.; Oliver J. McConnell, Wayne, Pa.; Robert R. West, Seattle; Theresa Martinez, Greenbank, both of Wash.

[73] Assignee: ZymoGenetics, Inc., Seattle, Wash.

[21] Appl. No.: 483,216

[22] Filed: Jun. 7, 1995

[51] Int. Cl.$^6$ .............. A61K 31/335; A61K 31/19; A61K 31/12; A61K 31/075

[52] U.S. Cl. ............... 514/450; 514/557; 514/570; 514/684; 514/690; 514/717; 514/719

[58] Field of Search ................... 514/450, 557, 514/570, 684, 690, 717, 719

[56] References Cited

U.S. PATENT DOCUMENTS 5,250,519  10/1993  Conrad et al. ............... 514/56

FOREIGN PATENT DOCUMENTS

568310A1  11/1993  European Pat. Off. .

OTHER PUBLICATIONS

Ostman et al., *J. Cell Biol.* 118: 509–519, 1992.
Kimura et al., *Japan. J. Pharmacol.* 59: 51–56, 1992.
Castellot et al., *J. Cell. Biol.* 109(6): 3147–3155, 1989.
Cavari et al., *Cell Biol. Intl.* 17(8): 781–786, 1993.
Reilly et al., *J. Cell. Phys.* 136: 23–32, 1988.
Guyton et al., *Circulation Research* 46(5): 625–634, 1980.
Popma et al., *Circulation* 84(3): 1426–1436, 1991.
Ferrell et al., *Circulation* 85(4): 1630–1631, 1992.
Lindner et al., *J. Clin. Invest.* 90: 2044–2049, 1992.
Jawien et al., *J. Clin. Invest.* 89: 507–511, 1992.
Lindner et al., *J. Clin. Invest.* 85: 2004–2008, 1990.
Currier et al., *JACC* 17: 118B–125B, 1991.
Schmid et al., *Seminars in Thrombosis and Hemostasis 19, Suppl. 1*: 155–159, 1993.
Edelman et al., *Proc. Natl. Acad. Sci. USA* 87: 3773–3777, 1990.
Rubin et al., *Lancet* Jun. 18, 1988: 1353–1356, 1988.
Buchwald et al., *Circulation* 86(2): 531–537, 1992.

*Primary Examiner*—Kimberly Jordan
*Attorney, Agent, or Firm*—Gary E. Parker; Debra K. Leith; Deborah A. Sawislak

[57] ABSTRACT

Methods for inhibiting intimal hyperplasia in the vasculature of mammals, including primates, are disclosed. The methods comprise administering to the mammal an effective amount of Brefeldin A or a derivative of Brefeldin A. The methods are useful in reducing intimal hyperplasia due to, for example, vascular injuries resulting from angioplasty, endarterectomy, reduction atherectomy or anastomosis of a vascular graft. The non-peptide PDGF antagonists Brefeldin A and its derivatives may optionally be administered coordinately with heparin, whereby the coordinately administered of non-peptide PDGF antagonist and heparin are combinatorially effective in inhibiting intimal hyperplasia.

20 Claims, No Drawings

PDGF ANTAGONISTS III

BACKGROUND OF THE INVENTION

Proliferation of smooth muscle cells (SMCs) in the vessel wall is an important event in the formation of vascular lesions in atherosclerosis, after vascular reconstruction or in response to other vascular injury. For example, treatment of atherosclerosis frequently includes the clearing of blocked vessels by angioplasty, endarterectomy or reduction atherectomy, or by bypass grafting, surgical procedures in which atherosclerotic plaques are compressed or removed through catheterization (angioplasty), stripped away from the arterial wall through an incision (endarterectomy) or bypassed with natural or synthetic grafts. These procedures remove the vascular endothelium, disturb the underlying intimal layer, and result in the death of medial SMCs. This injury is followed by medial SMC proliferation and migration into the intima, accompanied by excessive deposition of extracellular matrix. This lesion development characteristically occurs within the first few weeks and up to six months after injury and stops when the overlying endothelial layer is reestablished. In humans, these lesions are composed of about 20% cells and 80% extracellular matrix.

In about 30% or more of patients treated by angioplasty, endarterectomy or bypass grafts, thrombosis and/or SMC proliferation in the intima causes re-occlusion of the vessel and consequent failure of the reconstructive surgery. This closure of the vessel subsequent to surgery is known as restenosis.

A similar process of SMC proliferation has also been observed in organ transplants, and may contribute to transplant atherosclerosis and organ failure. The intimal thickening in this process involves only the grafted organ.

It has been postulated that platelet mitogens, such as platelet derived growth factor (PDGF), play a role in the development of atherosclerotic plaques (see Ross et al., *Cell* 46: 155–169, 1986; Harker, *Am. J. Cardiol.* 60: 20B–28B, 1987). One proposed mechanism for plaque formation is the release by platelets, at sites of endothelial denudation, of growth factors that stimulate SMC growth (Ross and Glomset, *N. Eng. J. Med.* 295: 369–377, 420–425, 1976; Ross, *Arteriosclerosis* 1: 293–311, 1981). Moore et al. (*Thrombos. Haemostas. (Stuttg.)* 35: 70, 1976) and Friedman et al. (*J. Clin. Invest.* 60: 1191–1201, 1977), using an indwelling catheter injury model, reported an inhibition of experimentally induced intimal lesion formation in rabbit arteries by prolonged thrombocytopenia induced by administration of anti-platelet serum. It has also been postulated that SMCs may themselves produce PDGF which stimulates lesion development through an autocrine mechanism (Ross et al., ibid; Walker et al., *Proc. Natl. Acad. Sci. USA* 83: 7311–7315, 1986). Fingerle et al. (*Proc. Natl. Acad. Sci. USA* 86: 8412–8416, 1989) investigated intimal lesion formation in thrombocytopenic rats and concluded that platelets do not play a role in the initial SMC proliferation after balloon injury but may regulate SMC migration into the intima. Platelets are now known to release a number of growth factors, including PDGF, epidermal growth factor (EGF), transforming growth factors alpha and beta (TGFα and TGFβ), insulin-like growth factor I (IGF-I) and platelet derived endothelial cell growth factor, as well as several chemoattractant molecules. Although certain studies implicate PDGF in processes associated with lesion development, the etiology of intimal hyperplasia in primates, remains undefined.

Removal of atherosclerotic plaques by angioplasty or endarterectomy has limited efficacy, and no effective treatment for restenosis of treated vessels or stenosis of bypass grafts has been developed. There is therefore a need in the art for methods of reducing or preventing the development of SMC-rich lesions in vascular walls, including stenosis of blood vessels following vascular injury, such as injury due to balloon catheterization, endarterectomy, endovascular stent emplacement, or reduction atherectomy, as well as in vascular grafts, organ transplants and catheter emplacements. The present invention provides such methods and fulfills other, related needs.

SUMMARY OF THE INVENTION

The present invention provides methods for using Brefeldin A (1,6,7,8,9,11a,12,13,14,14a-Decahydro-1,13-dihydroxy-6-methyl-4H-cyclopent[f]oxacyclotridecin-4-one) and derivatives thereof as non-peptide PDGF antagonists.

The invention provides methods of inhibiting intimal hyperplasia in the vasculature of a mammal comprising administering an antihyperplastically effective amount of a compound of formula I, II, or III:

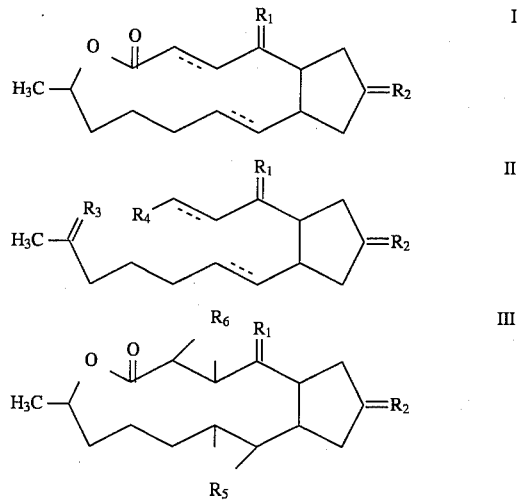

Within the structures I, II, and III the dotted line indicates a single or double bond; $R_1$ and $R_2$ are the same and are the single group O, or H and OH, H and OR, or H and OCOR; $R_3$ is the single group O, or H and OH, H and OR, or H and OCOR; $R_4$ is COOH, a pharmaceutically acceptable salt of COOH, or $CH_2OR$; $R_5$ and $R_6$ are both oxygen or one of $R_5$ and $R_6$ is O and the other comprises a double bond; and R is $C_{1-5}$ alkyl, phenyl or benzyl.

Preferred compounds for use within the present invention include those in which the dotted line indicates a single or double bond, $R_1$ and $R_2$ are the single group O, or H and OH; those in which the dotted line indicates a single or double bond, and $R_1$ and $R_2$ are H and OR, or H and OCOR, wherein R is C1–5 alkyl, phenyl or benzyl; those in which $R_1$ and $R_2$ are the single group O, or H and OH, $R_5$ is O and $R_6$ is single or double bond; those in which $R_1$ and $R_2$ are the single group O, or H and OH, $R_5$ is a single or double bond, and $R_6$ is O; those in which the dotted line indicates a single or double bond, $R_1$, $R_2$ and $R_3$ are the single group O, or H and OH, and $R_4$ is COOH or a pharmaceutically acceptable salt of COOH; and those in which the dotted line indicates a single or double bond, $R_1$, $R_2$ and $R_3$ are H and OR, or H and OCOR; $R_4$ is $CH_2OR$; and R is C1–5 alkyl, phenyl, or benzyl.

In a preferred embodiment the invention provides a method for inhibiting intimal hyperplasia in a mammal by administering an antihyperplastically effective amount of Brefeldin A.

The invention further provides methods for inhibiting intimal hyperplasia in a mammal, wherein said intimal hyperplasia results from acute vascular injury, emplacement of a vascular graft or transplanted organ.

The invention also provides methods for inhibiting intimal hyperplasia at a site of vascular injury in a mammal. Within selected embodiments of the invention, the vascular injury is due to vascular reconstruction, such as angioplasty, endarterectomy, reduction atherectomy, endovascular laser ablation or anastomosis of a vascular graft.

The invention also provides methods for administration of a compound of formula I, II or III within a hyperplastically effective time period prior to, concurrent with or subsequent to an acute vascular injury in a mammal. Within a related embodiment, the compound is administered concurrently with, or within an antihyperplastically effective time period before, an acute vascular injury in a mammal.

The invention further provides methods of inhibiting intimal hyperplasia in a mammal by coordinate administration of a compound of formula I, II or III with heparin.

The invention also provides methods for using compounds of formula I, II or III as PDGF antagonists, such as for inhibiting PDGF activity in a mammal.

DETAILED DESCRIPTION OF THE INVENTION

As noted above, restenosis of blood vessels is a common problem in patients who have undergone angioplasty, endartarectomy, or bypass grafting. Restenosis is one example of intimal hyperplasia, which is believed to proceed via a process that includes both proliferation (mitosis) and migration of vascular smooth muscle cells in the area damaged by the surgical procedure, as well as by the production (deposition) of extracellular matrix. See, in general, Harker, *Am. J. Cardiol.* 60:20B–28B, 1987; and DeFeudis, *Drug News and Perspectives* 5:49–51, 1992. This proliferative process is also manifested in the occlusion of vascular grafts (both natural, including autologous and allogeneic, and synthetic), and in transplanted organs. This proliferative process results in the development of lesions rich in smooth muscle cells and is referred to herein as intimal hyperplasia.

The present invention provides methods for inhibiting the development of SMC-rich lesions (partial or complete blocking of a blood vessel through intimal thickening (hyperplasia)) through the use of a antihyperplastically effective amount of a compound of formula I, II or III. These compounds have been found to be non-peptide PDGF antagonists. The compounds may be used either independently or in combination with an antihyperplastically effective amount of heparin. The present invention also provides methods for using Brefeldin A and derivatives thereof as non-peptide PDGF antagonists. Non-peptide PDGF antagonists may be useful as therapeutics in a treatment regime for scleroderma, lung hyperplasia, kidney fibrosis, rheumatoid arthritis or in treatment of solid cancers, including, but not limited to, osteosarcoma, fibrosarcoma, glioma or other proliferative cellular diseases.

Derivatization methods used to produce the compounds of the invention are well known in the art. R. C. Larock, *Comprehensive Organic Transformations*, VCH Publishers, Inc., New York, 1989; H. O. House, *Modern Synthetic Reactions*, W. A. Benjamin, Inc., Menlo Park, Calif. 1972; L. F. Fieser and M. Fieser, *Reagents for Organic Synthesis*, John Wiley and Sons, Inc., New York Vol. 1, 1967; J. March, *Advanced Organic Chemistry: Reactions, Mechanisms, and Structure*, McGraw-Hill Book Company, New York, 1968,; I. T. Harrison and S. Harrison, *Compendium of Organic Synthetic Methods*, Wiley-Interscience, New York; Vol. 1, 1971; P. N. Rylander, *Hydrogenation Methods*, Academic Press, New York, 1985; D. J. Pasto and C. R. Johnson, *Organic Structure Determination*, Prentice-Hall, Inc. Englewood Cliffs, N.J., 1969.

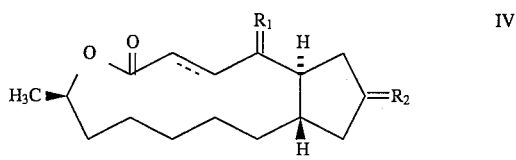

IV

Brefeldin A derivatives of formula IV can be prepared by selectively reducing the olefin that is part of the α,β-unsaturated ketone with sodium borohydride at low temperatures or in pyridine, lithium in ammonia-ether, or zinc in acetic acid. Hydrogenation using hydrogen and a catalyst, preferably palladium or carbon, results in reduction of both double bonds. Oxidation of the hydroxyl functionalities to carbonyls is accomplished using chromium reagents, for examples, chromic trioxide and sulfuric acid (Jones' reagent) or pyridinium chlorochromate, or using dimethylsulfoxide and acetic anhydride. Reduction and oxidation can be carried out selectively.

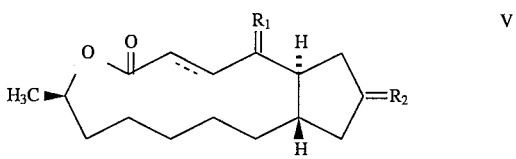

V

Brefeldin A derivatives of formula V are prepared by acylating the hydroxyls using an appropriate acid chloride or anhydride and a base, preferably pyridine. Conversion of hydroxyls to ethers can be accomplished with a base or silver oxide and an appropriate alkyl or benzyl halide. Reduction of the double bonds is as described above.

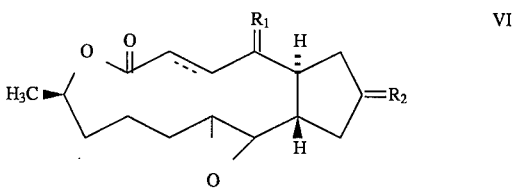

VI

Brefeldin A derivatives of formula VI are prepared by epoxidizing the isolated double bond using 4-chloroperoxybenzoic acid in a halogenated solvent, e.g., dichloromethane. Oxidation of the hydroxyls and reduction of the conjugated double bond are as described above.

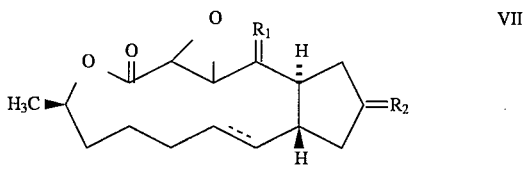

VII

Brefeldin A derivatives of formula VII are prepared by epoxidation of the olefin conjugated with the ester carbonyl with hydrogen peroxide under basic conditions. Oxidation of the hydroxyls and reduction of the double bond are as described above.

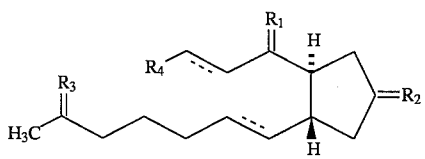

VIII

Brefeldin A derivatives of formula VIII are prepared by reduction of the double bonds and oxidation of the hydroxyls as described above. Hydrolysis of the lactone group is accomplished using potassium or sodium hydroxide in an alcohol, such as methanol.

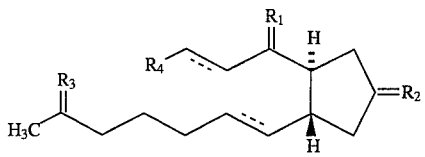

IX

Brefeldin A derivatives of formula IX are prepared by (selective) reduction of the double bonds and formation of acyl or alkyl derivatives of the hydroxyl functionalities as described above. Formation of the tetrahydroxy derivatives is accomplished using metal hydride reducing agents, preferably lithium aluminum hydride.

As used herein, the term "non-peptide PDGF antagonist" refers to a compound, other than a peptidic compound, that inhibits a PDGF-induced stimulation of a response pathway. A "response pathway" is a biochemical pathway activated in response to external stimuli that is generally, but no always, directly coupled to a membrane-bound receptor. Response pathways generally induce cellular responses such as extracellular matrix secretion from responsive cell lines, hormone secretion, chemotaxis, differentiation, or the stimulation of cell division of responsive cells.

PDGF receptors are integral, transmembrane glycoproteins whose expression is generally limited to cells of mesodermal origin. Two PDGF receptor polypeptides have been described. These are termed "alpha receptor" (Kelly et al., WO 90/14425; Kelly et al., U.S. Pat. No. 5,371,205; Claesson-Welsh et al., *Proc. Natl. Acad. Sci. USA* 86: 4917–4921, 1989) and "beta receptor" (Claesson-Welsh et al., *Mol. Cell. Biol.* 8: 3476–3486, 1988; Gronwald et al., *Proc. Natl. Acad. Sci. USA* 85: 3435–3439, 1988). In the presence of PDGF ligand, the receptor polypeptides dimerize. Three receptor subtypes are thus possible: αα, αβ, and ββ. The β receptor is specific for the B-chain of PDGF, while the α receptor binds the A-chain and the B-chain. Consequently, the growth regulatory responsiveness of cells to PDGF depends not only on the availability of PDGF AA, AB and BB ligand isoforms, but also on the expression and availability of different PDGF receptor subtypes (Heldin et al., *Cell Regul.* 1: 555–566, 1990). Human smooth muscle cells express both α and β receptor subtypes (Heldin et al., *Cell Regul.* 1: 555–566, 1990), but other cell types are known which express only a single receptor subtype (Gronwald et al., *J. Biol. Chem.* 264: 8120–8125, 1989).

The current invention also provides methods for inhibition of intimal hyperplasia by coordinately administering an antihyperplastically effective amount of a non-peptide PDGF antagonist and an antihyperplastically effective amount of heparin. As used herein, the term "heparin" refers to any member of a family of structurally complex, sulphated glycosaminoglycans generally characterized by a structure of repeating glucosamine and glucuronic acid sugar residues (Casu, *Adv. Carbohyd. Chem. and Biochem.* 47: 578–583, 1985). The most widely known heparin is "unfractionated" or "commercial" heparin prepared from bovine lung or porcine gut, which encompasses a heterogeneous mixture of heparin molecules ranging from approximately 8,000 to 20,000 daltons molecular weight (Wolinsky et al., *J. Am. Coll. Cardiol.* 15: 475–481, 1990). However, the term heparin also encompasses a broad range of more homogeneous heparin preparations, as well as heparin-like molecules, including heparan sulfates. Among these particular heparin examples, more specific heparin subtypes are also known. For example, heparan sulfate moieties produced by endothelial cells (Castellot et al., *J. Cell. Biol.* 90: 372–379, 1981) and smooth muscle cells (Fritze et al., *J. Cell. Biol.* 100: 1041–1049, 1985) have been isolated which are reportedly up to 40 times more active than unfractionated heparin for inhibiting proliferation of smooth muscle cells. In addition, among the naturally occurring heparin size variants, fractionated heparin species that exhibit predominantly either anticoagulant or antiproliferative activity have been isolated (Wolinsky et al., *J. Am. Coll. Cardiol.* 15: 475–481, 1990). The latter activity tends to be present in the low molecular weight heparin species, such as heparins in the range of penta- to decasaccharides, which have been reported to also provide greater bioavailability and a longer half-life (Id., Bacher et al., *Thrombosis Res.* 70: 295–306, 1993), and may therefore be particularly useful within specific embodiments of the invention. Also included within the definition of heparin for the purposes of describing the invention are synthetic heparins and heparin derivatives, a variety of which have been produced using conventional chemical synthetic, modifying and degradative techniques (see for example, Roden, L. *The Biochemistry of Glycoproteins and Proteoglycans* (Lennarz, W. J., ed.) pp 267–371, Plenum Publishing Corp., New York, 1980, incorporated herein by reference).

An "antihyperplastically effective amount" of a compound is defined as an amount of a compound sufficient to measurably reduce or prevent intimal hyperplasia in a blood vessel, vessel graft or vascular component of a transplanted organ. More specifically, "inhibition of intimal hyperplasia" is herein defined to include any measurable inhibition of one or more of the intimal hyperplastic processes described in the art, such as vascular smooth muscle cell (VSMC) migration, VSMC proliferation, and neointimal deposition of extracellular matrix. In this context, reduction or prevention of intimal hyperplasia, or of a hyperplastic process involved in intimal hyperplasia, can be readily evaluated using in vitro, in vitro and in vivo assay systems known in the art, in particular primate-based assay systems (e.g., non-human or human primate VSMC cultures or vascular tissue explants, or non-human primate in vivo tests). By preventing PDGF from exerting its stimulatory effect, SMC proliferation and subsequent matrix deposition may be reduced. A reduction in intimal hyperplasia is clinically manifested as a significant decrease in loss of lumenal volume after an acute vascular injury. Such a reduction will generally result in a decreased need for re-vascularization procedures (e.g., repeat angioplasty) at the site of the initial injury.

The methods of the present invention are particularly useful in the treatment of intimal hyperplasia due to acute vascular injury. Acute vascular injuries are those which occur rapidly (i.e. over days to months), in contrast to chronic vascular injuries (e.g. atherosclerosis) which develop over a lifetime. Acute vascular injuries often result from surgical procedures such as vascular reconstruction, wherein the techniques of angioplasty, endartarectomy, reduction atherectomy, endovascular stenting, endovascular laser ablation, anastomosis of a vascular graft or the like are employed. Hyperplasia may also occur as a delayed response in response to, e.g., emplacement of a vascular graft or organ transplantation.

The compounds of formulas I, II and III are administered to mammals at risk for intimal hyperplasia or otherwise in need of PDGF antagonist therapy in amounts effective to inhibit hyperplastic processes or other biological effects of PDGF. In general, the compounds will be administered at from 1 µg to 10 mg of compound per kg of recipient weight per day, more commonly less than 1 mg/kg/day, depending upon such factors as the specific activity of the particular compound; the age, weight, and general condition of the patient; and the severity of the condition to be treated. Life-threatening conditions will in general be treated with large doses that would be otherwise unacceptable. Doses for specific compounds may be determined from in vitro or ex vivo studies in combination with studies on experimental animals. Concentrations of compounds found to be effective in vitro or ex vivo provide guidance for animal studies, wherein doses are calculated to provide similar concentrations at the site of action. Doses determined to be effective in experimental animals are generally predictive of doses in humans within one order of magnitude. Determination of dose is within the level of ordinary skill in the art, and the ultimate dose used in a particular setting will be determined by the clinician.

In humans treated with non-peptide PDGF antagonist therapy, either alone, or in combination with heparin, the antagonist may be given under a wide range of conditions. The antagonist can be given via bolus injections, both prior to the re-vascularization procedure as well as multiple times following the procedure. The antagonist may be given as a bolus injection (intravenous, intramuscular, intraperitoneal or subcutaneous) prior to the procedure (generally within 24 hours before surgery) and a constant infusion following the procedure (including infusion via implanted pumps). In many cases it will be preferable to administer daily doses (including administration by infusion) during a hospital stay, followed by less frequent bolus injections during a period of outpatient treatment of one to two weeks or more. Treatment may be continued for up to six months after initial injury. The antagonist may be given via multiple routes including intravenous, intramuscular or subcutaneous injections. In addition the antagonist may be delivered locally to the site of vascular injury using perfusion balloon catheters, coating onto stents, or placement on gel coated balloons. In the latter cases it would be expected that the doses of antagonist would be substantially less than that required when given systemically. The antagonist may also be delivered by slow-release delivery systems, including such systems incorporated into vascular grafts or stents, or by way of perfusion or double balloon catheters. Pumps and other known delivery systems may also be employed.

In an alternate embodiment of the invention, a non-peptide PDGF antagonist is administered to a mammal coordinately with heparin, in respective unit doses of antagonist and heparin sufficient to combinatorially inhibit intimal hyperplasia in the vasculature of the mammal. In this context, "coordinate administration" is intended to include concurrent, separate or sequential administration of the antagonist and heparin, wherein both the antagonist and heparin are administered within a limited, combinatorially effective time period relative to one another. A "combinatorially effective time period" is defined as a maximum intervening time period between administration of the antagonist and administration of the heparin in which the two agents are combinatorially effective in inhibiting the hyperplasia. The term "combinatorially effective" is in turn defined as producing a measurable inhibition of intimal thickening or lesion formation, or of a hyperplastic process, which exceeds a maximum level of inhibition independently provided by either the antibody or heparin administered alone, under otherwise comparable conditions and dose.

Generally, doses of heparin will be between approximately 1 µg–100 mg/kg/day. Preferably, heparin doses will be between 20 µg–10 mg/kg/day, and more preferably less than about 1 mg/kg/day. Those skilled in the art will recognize that actual doses will be determined with consideration of specific circumstances, including patient parameters and the characteristics of the antagonist(s) (e.g., specificity, specific activity, circulating half-life) and heparin (e.g., antithrombotic activity) administered.

The inhibition of hyperplasia will be expected to lead to a decrease in clinical events in patients. These events include a decrease in one or more of myocardial infarcts, angina, the need for revasculariztion procedures, and death.

The following examples are offered by way of illustration, not by way of limitation.

EXAMPLE 1

Antagonist Assay

Initial characterization of Brefeldin A as a non-peptide PDGF antagonist was made possible through an SRE-Luciferase high through-put assay system which identifies substances that are able to block expression of a serum response element (SRE)-luciferase reporter gene expressed in SWISS3T3 cells. The SRE-luciferase construct, pKZ67, is a pUC18-derived mammlian cell expression vector comprising a luciferase expression unit that includes a synthesized segment containing human c-fos sequence from −360 to +30 (van Straaten et al., *Proc. Natl. Acad. Sci. USA* 80:3183–3187, 1983) (including TATA, SRE and SIE promoter elements), a luciferase sequence (Delegeane et al., *Mol. Cell Biol.* 7:3994–4002, 1987; deWet et al., *Mol. Cell Biol.* 7:725–737, 1987), and a human growth hormone gene terminator. This expression unit is in opposite transcriptional orientation to a second expression unit that includes a neomycin resistance marker flanked by SV40 promoter and terminator sequences. SWISS3T3 cells express endogenous growth factor receptors for PDGF-AA, -AB and -BB; bFGF and EGF. Stimulating the receptors with any of these growth factors initiates a signal cascade leading to induction of luciferase. PMA (phorbol 12-myristate 13-acetate) by passes the receptor and initiates an internal signal cascade by stimulating protein kinase C leading to the induction of luciferase. The degree of antagonist specificity can be determined by comparing the resultant signal for the three growth factors (PDGF, bFGF, and EGF). Compounds resulting in a 50-fold signal reduction compared to the control were considered for further analysis.

SWISS3T3/KZ67-G1-6 cells (transfected with a SRE-luciferase reporter gene) were maintained by serial passage in maintenance medium (DMEM (GIBCO BRL, Gaithersburg, Md.) supplemented with 10% fetal bovine serum (FBS), 2 mM L-glutamine, 1 mM sodium pyruvate, 1 mg/ml G418). Two days prior to assay, cells were trypsinized, adjusted to $5 \times 10^4$ cells/well in growth medium (DMEM supplemented with 1% FBS, 2 mM L-glutamine, 1 mM sodium pyruvate), plated in opaque white 96 well micortiter plates at 200 μl/well (1×10⁴ cells/well) and grown for 48 hours at 37° C., 5% $CO_2$.

Test substances were prepared in 4% DMSO. Induction was initiated by removing spent medium from the wells and adding 50 μl/well assay medium (Ham's F12 (GIBCO BRL) supplemented with 0.5% Fraction V BSA (Sigma, St. Louis, Mo.), 2 mM L-glutamine, 1 mM sodium pyruvate, 20 mM Hepes. Test samples were added in 25 μl assay medium. Controls, prepared in assay medium, were included on each plate: untreated wells (basal), 12.5 ng/ml, more preferrably 6.25 ng/ml, PDGF BB (platelet derived growth factor, stock 10 μg/ml 10 mM Acetic acid, 0.25% RSA in PBS), 2.0 ng/ml bFGF (basic fibroblast growth factor (Genzyme Diagnostics, Cambridge, Mass.)), 4.5 ng/ml EGF (epidermal growth factor (Sigma)) or 50 ng/ml PMA (Sigma). Final assay concentration of DMSO do not exceed 1%. Plates were incubated for 5 hours at 37° C., 5% $CO_2$.

Folowing induction, luciferase activity was measured using a Promega luciferase assay kit (E1500; Promega Corp., Madison, Wis.) according to the assay kit protocol. Briefly, assay medium was removed from the plate, and 25 μl/well cell lysis buffer, diluted 1:5 with sterile water, was added to the plate. Plates were incubated for 15 minutes. The plates were transferred to a Lumiskan™ microtiter luminometer (ICN Biomedical, Cleveland, Ohio), which added 40 μl/well Luciferase Assay substrate (Promega Corp.). The amount of luminescence (relative light units, RLU) was determined following a 1 second mix and a 1–3 integration of signal. Basal (uninduced) luciferase signal was substracted from all measurements, and the luciferase signal induced by test samples was expressed as a percentage of the signal from the controls. Samples inducing a signal over the basal level were selected for further characterization. The data presented in Table 1 show the approximate effective dose of Brefeldin A required to inhibit 50% of the control activity ($IC_{50}$).

TABLE 1

| PDGF $EC_{50}$ (μM) | bFGF $EC_{50}$ (μM) | EGF $EC_{50}$ (μM) | PMA $EC_{50}$ (μM) |
|---|---|---|---|
| 0.4 | No activity | No activity | 0.4 |

EXAMPLE 2

Inhibition of $^{125}$I-PDGF-BB Binding to Rat Smooth Muscle Cells (SMCs)

Brefeldin A was analyzed for the ability to inhibit $^{125}$I-PDGF-BB binding to monolayers of rat SMCs. SMCs were plated at approximately 20,000 cells/well in 24-well culture dishes. The cells were used for assay 2–7 days after plating. The test compound was diluted in binding media (500 ml Hams F-12 (Gibco BRL), 12 ml 1M Hepes pH 7.4, 5 ml 100X PSN, 1 gm rabbit serum albumin (Sigma Chemical Co., St. Louis, Mo.) to the concentrations shown in Table 2, then added to the SMCs (1 ml/well) in triplicate. To the wells was then added 50 μl of a $^{125}$I-PDGF-BB binding stock solution. Binding media alone was used as the negative control, and the addition of 200 ng/ml of PDGF-BB was used to determine nonspecific binding for $^{125}$I-PDGF-BB. The cells were incubated for approximately 1½ hours at 4° C., then washed with binding media to remove unbound ligand. The cells were then incubated with extraction buffer (20 mM Tris-HCl pH 8.0, 100 mM NaCl, 1 mM EDTA, 0.5% sodium deoxycholate, 10 mM NaI, 1% bovine serum albumin), and the extracts were harvested and counted in a gamma counter.

The results of the binding studies are shown in Table 2. The data are presented as specific cpm bound for $^{125}$I-PDGF-BB. Nonspecific binding, determined by the addition of 200 ng/ml of unlabeled PDGF-BB, was 853 cpm, and has been subtracted from the data presented.

TABLE 2

Inhibition of $^{125}$I-PDGF-BB Binding to Rat SMCs

| Compound | Concentration (μM) | $^{125}$I PDGF-BB Bound (CPM) | % Control Binding |
|---|---|---|---|
| Brefeldin A | 100 | 8879 | 89 |
|  | 50 | 9199 | 92 |
| Negative Control |  | 10006 | 100 |

EXAMPLE 3

Inhibition of PDGF-BB Mitogenic Activity on Baboon Smooth Muscle Cells

Brefeldin A was analyzed for the ability to inhibit the mitogenic activity of PDGF on baboon smooth muscle cells. All mitogenesis assays performed on baboon vascular smooth muscle cells (BVSMCs) were done on primary cultures of cells between passages 13 and 20 in culture. The initial cultures were established from outgrowth of aortic tissue explants. Baboon smooth muscle cells were plated at approximately 20,000 cells per well, in DMEM supplemented with 10% fetal calf serum, into 24-well culture dishes. One day prior to use the culture media was removed, and 1 ml of Mito Media (Table 3) was added to each well to allow the cells to become quiescent. At the time of the experiment the cells were stimulated with PDGF-BB. A standard curve was run for PDGF-BB with concentrations of 1, 0.5, 0.25, 0.062, and 0 ng/ml. 20X stock solutions were made for each of the PDGF concentrations by dilution in 10 mM acetic acid containing 0.25% albumin, and 50 μl of PDGF or dilution vehicle alone was added to the culture wells.

TABLE 3

Mito Media

For a 500 ml solution:

| | |
|---|---|
| 250 ml | DMEM (GIBCO BRL) |
| 250 ml | Ham's F-12 (GIBCO BRL) |
| 0.25 ml | 10 mg/ml stock of insulin (GIBCO BRL) to give a final concentration of 5 μl/ml |
| 1 ml | 10 mg/ml stock of transferrin (Collaborative Research, Bedford, MA) to give a final concentration of 20 μl/ml |
| 2 ml | 4 μg/ml stock of selenium (Aldrich Chemical, Milwaukee, WI) to give a final concentration of 5 nM |
| 5 ml | 10% stock solution of bovine serum albumin (GIBCO BRL)to give a final concentration of 0.1%. |

To analyze the activity of Brefeldin A to neutralize PDGF-BB mitogenic activity, 1 ng/ml of PDGF was added to wells along with dilutions of Brefeldin A. The cells were incubated with the test samples for approximately 20 hours at 37° C. Fifty μl of a 20x stock solution was then added to each well to give a final concentration of 1 μCi/ml. The cells were incubated for 4 hours at 37° C., washed with PBS, then harvested with trypsin and counted for [³H] thymidine incorporation in a Wallac (Turku, Finland) Betaplate™ liquid scintillation counter. The results, presented in Table 3, demonstrate that PDGF-BB mitogenic activity was inhibited by Brefeldin A in a dose dependent fashion. The ED₅₀ for the inhibition was approximately 25 nM for Brefeldin A.

TABLE 4

Inhibition of PDGF-BB Mitogenic Activity on Baboon Smooth Muscle Cells

| Compound | Conc. | ³H Thymidine (CPM Incorporated) | |
|---|---|---|---|
| | | (−) Heparin | (+) 0.5 U/ml Heparin |
| PDGF-BB (1 ng/ml)/ Brefeldin-A | 100 nM | 39 | 31 |
| | 50 | 36 | 44 |
| | 25 | 798 | 684 |
| | 12.5 | 1293 | 854 |
| | 0 | 1701 | 1089 |
| PDGF-BB | 1 ng/ml | 1701 | |
| | 0.5 | 959 | |
| | 0.25 | 392 | |
| | 0.125 | 226 | |
| | 0.062 | 120 | |
| | 0 | 74 | |

These data demonstrate that doses of Brefeldin A 1000-fold lower than those required to inhibit PDGF binding to rat SMCs are able to significantly inhibit PDGF-BB mitogenic activity on baboon smooth muscle cells.

As part of this same experiment, the inhibitory potency of Brefeldin A was analyzed in the presence of heparin to determine if heparin is able to act in a combinatorial manner with Brefeldin A for inhibiting PDGF-BB mitogenic activity. Baboon smooth muscle cells were incubated in Brefeldin A with 1 ng/ml PDGF-BB in the presence of 0.5 U/ml of unfractionated heparin. The cells were pulse-labeled with [³H] thymidine as described above, and the level of [³H] thymidine incorporation was determined. The results, presented in Table 3, demonstrate that the addition of heparin to Brefeldin A led to a further inhibition of [³H] thymidine above that achieved by Brefeldin A alone.

We claim:

1. A method of inhibiting intimal hyperplasia in the vasculature of a mammal comprising administering to said mammal an antihyperplastically effective amount of a compound of formula I, II, or III:

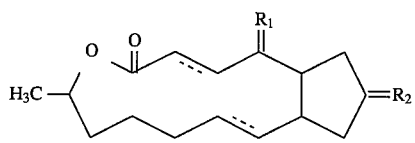

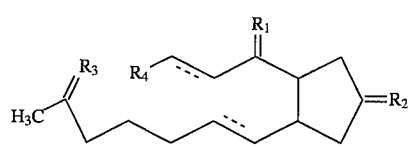

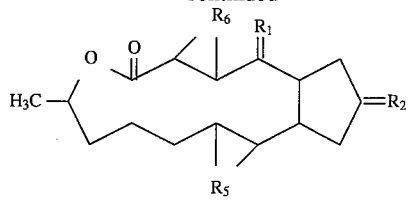

wherein the dotted line indicates single or double bond;

$R_1$ and $R_2$ are the same and are the single group O, or H and OH, H and OR, or H and OCOR;

$R_3$ is the single group O, or H and OH, H and OR, or H and OCOR;

R4 is COOH, a pharmaceutically acceptable salt of COOH, or $CH_2OR$;

$R_5$ and $R_6$ are both oxygen or one of $R_5$ and $R_6$ is O and the other comprises a double bond; and R is $C_{1-5}$ alkyl, phenyl or benzyl.

2. A method according to claim 1 wherein said compound is a compound of formula IV wherein

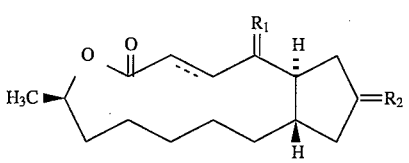

the dotted line indicates a single or double bond; and $R_1$ and $R_2$ are the single group O, or H and OH.

3. A method according to claim 1 wherein said compound is a compound of formula V

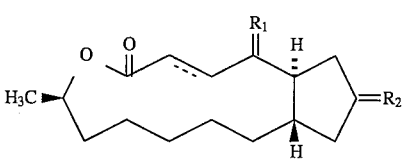

wherein the dotted line indicates a single or double bond; and

R1 and R2 are H and OR, or H and OCOR, wherein R is a C1–5 alkyl, phenyl or benzyl.

4. A method according to claim 1 wherein said compound is a compound of formula VI:

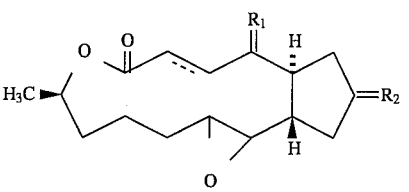

wherein the dotted line indicates a single or double bond; and $R_1$ and $R_2$ are the single group O, or H and OH; and $R_5$ is O.

5. A method of claim 1 wherein the compound is a compound of formula VII:

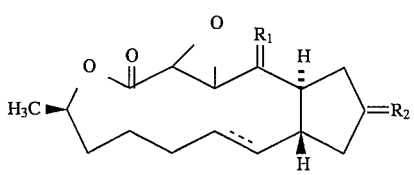

wherein the dotted line indicates a single or double bond; $R_1$ and $R_2$ are the single group O, or H and OH; and $R_6$ is O.

6. A method according to claim 1 wherein said compound is a compound of formula VIII:

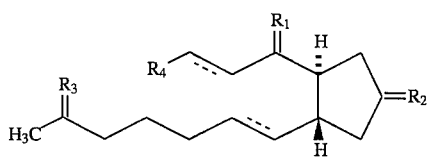

wherein the dotted line indicates a single or double bond; $R_1$, $R_2$ and $R_3$ are the single group O, or H and OH; and $R_4$ is COOH, or a pharmaceutically acceptable salt of COOH.

7. A method according to claim 1 wherein said compound is a compound of formula IX:

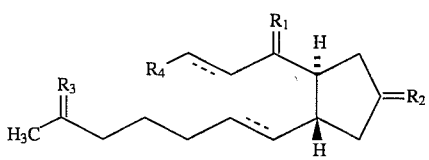

wherein the dotted line is a single or double bond; R1, R2, and R3 are H and OR, or H and OCOR, wherein R is a C1–5 alkyl, phenyl or benzyl; and R4 is CH2OR.

8. A method according to claim 1 wherein said compound is Brefeldin A:

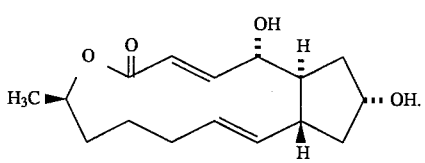

9. A method according to claim 1 wherein said mammal is a primate.

10. A method according to claim 1 wherein said compound is administered concurrently with, or within an antihyperplastically effective time period before, an acute vascular injury in said mammal.

11. A method according to claim 10 wherein said injury is due to vascular reconstruction.

12. A method according to claim 11 wherein said vascular reconstruction comprises angioplasty, endarterectomy, reduction atherectomy, endovascular laser ablation, endovascular stent emplacement, or anastomosis of a vascular graft.

13. A method according to claim 1 wherein compound is administered within an antihyperplastically effective time period following an acute vascular injury in said mammal.

14. A method according to claim 13 wherein said injury is due to vascular reconstruction.

15. A method according to claim 14 wherein said vascular reconstruction comprises angioplasty, endarterectomy, reduction atherectomy, endovascular laser ablation, endovascular stent emplacement, or anastomosis of a vascular graft.

16. A method according to claim 1 wherein said compound is administered concurrently with, or within an antihyperplastically effective time period before, emplacement of a vascular graft or transplanted organ.

17. A method according to claim 1 wherein said compound is administered within an antihyperplastically effective time following emplacement of a vascular graft or transplanted organ.

18. A method of inhibiting intimal hyperplasia in the vasculature of a mammal, comprising:

coordinately administering to said mammal an antihyperplastically effective amount of a non-peptide PDGF antagonist and an antihyperplastically effective amount of heparin, wherein said coordinately administered antigen and heparin are combinatorially effective to inhibit said hyperplasia.

19. A method according to claim 18, wherein said non-peptide PDGF antagonist and heparin are administered to said mammal by a mode of administration selected from the group consisting of oral, intravascular, perivascular, transdermal and rectal administration modes.

20. A method for inhibiting PDGF activity in a mammal, comprising administering to said mammal a PDGF-inhibiting amount of a compound of formula I, II, or III:

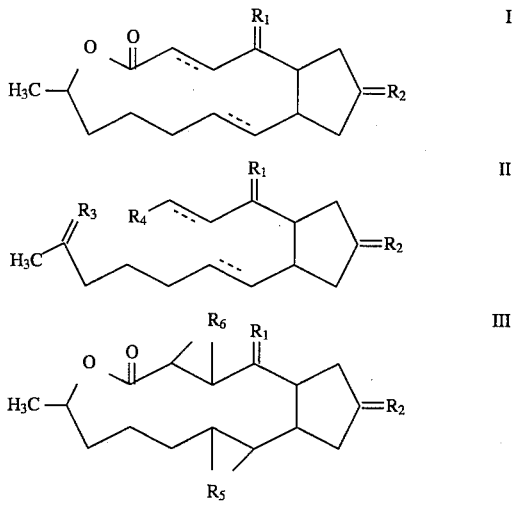

wherein the dotted line indicates single or double bond;

$R_1$ and $R_2$ are the same and are the single group O, or H and OH, H and OR, or H and OCOR;

$R_3$ is the single group O, or H and OH, H and OR, or H and OCOR;

R4 is COOH, a pharmaceutically acceptable salt of COOH, or $CH_2OR$;

$R_5$ and $R_6$ are both oxygen or one of $R_5$ and $R_6$ is O and the other comprises a double bond; and R is $C_{1-5}$ alkyl, phenyl or benzyl.

* * * * *

UNITED STATES PATENT AND TRADEMARK OFFICE
CERTIFICATE OF CORRECTION

PATENT NO. : 5,618,837
DATED : April 8, 1997
INVENTOR(S) : Hart et al.

It is certified that error appears in the above-identified patent and that said Letters Patent is hereby corrected as shown below:

In column 11, at line 44, please delete "Table 3" and insert thereof --Table 4--.

Signed and Sealed this

Second Day of June, 1998

Attest:

BRUCE LEHMAN

Attesting Officer     Commissioner of Patents and Trademarks